United States Patent
Choo et al.

(10) Patent No.: US 7,141,712 B2
(45) Date of Patent: Nov. 28, 2006

(54) RECOVERY OF PALM PHYTONUTRIENTS

(75) Inventors: Yuen May Choo, Selengor (MY); Harrison Lik Nang Lau, Selengor (MY); Chiew Wei Puah, Selengor (MY); Ah Ngan Ma, Selengor (MY); Yusof Basiron, Selengor (MY)

(73) Assignee: Malaysian Palm Oil Board, Selangor (MY)

( * ) Notice: Subject to any disclaimer, the term of this patent is extended or adjusted under 35 U.S.C. 154(b) by 437 days.

(21) Appl. No.: 10/642,597

(22) Filed: Aug. 19, 2003

(65) Prior Publication Data

US 2005/0101820 A1     May 12, 2005

(30) Foreign Application Priority Data

Jun. 20, 2002    (MY) ............................. PI 20023068

(51) Int. Cl.
    *C11B 3/00*        (2006.01)
    *C07C 403/00*     (2006.01)

(52) U.S. Cl. ...................... 585/864; 585/351; 554/207; 554/206

(58) Field of Classification Search ................ 585/351, 585/864; 554/207, 206
See application file for complete search history.

(56) References Cited

U.S. PATENT DOCUMENTS

| | | | | |
|---|---|---|---|---|
| 2,741,644 | A | * | 4/1956 | Blaizot .......................... 203/38 |
| 5,019,668 | A | * | 5/1991 | Keat et al. ................... 585/864 |
| 6,072,092 | A | * | 6/2000 | Ooi et al. .................... 585/351 |
| 6,649,781 | B1 | * | 11/2003 | Tou .............................. 554/207 |

* cited by examiner

*Primary Examiner*—Tam M. Nguyen
(74) *Attorney, Agent, or Firm*—Birch, Stewart, Kolasch & Birch, LLP.

(57) ABSTRACT

A process for the recovery of phytonutrients such as carotenes, phospholipids and ubiquinones from palm oil esters is disclosed. This process comprises the steps of vacuum distillation, treatment and purification of concentrate containing these phytonutrients. The alkyl esters is subjected to at least one stage vacuum distillation at temperature from 80° C. to 220° C. and pressure less than 40 mTorr. The carotenes concentrate is subjected to various physical and chemical treatments to yield higher carotenes concentration enriched with ubiquinones in indigenous diacylglycerols.

10 Claims, No Drawings

RECOVERY OF PALM PHYTONUTRIENTS

This nonprovisional application claims priority under 35 U.S.C. 119(a) on patent application No(s). PI 20023068 filed in Malaysia on Aug. 20, 2002, which is(are) herein incorporated by reference.

FIELD OF INVENTION

This invention relates to a process of recovery of phytonutrients such as carotenes, phospholipids and ubiquinones using vacuum distillation, various physical and chemical treatments and purification of the phytonutrients containing natural esterified oils and fats and has particular but not exclusive application to their recovery from palm oil.

BACKGROUND ART

Carotenoids are the natural pigments, which impart a rich orange-red colour in plants and animals. Carotenoids are found in abundance (~600 types) in nature. These include beta-carotene and alpha-carotene, which can be converted into Vitamin A (retinal) in the body. Other non-vitamin A carotenoids includes lycopene and phytoene. All these are present in crude palm oil. In fact, crude palm oil is one of the richest natural plant sources with carotenes with concentration of 500–700 ppm. Carotenoids have a number of important physiological properties. For example lycopene suppresses the growth of various cancer lines. These include the lung and liver cancer as well as colon tumours.

Ubiquinone (Coenzyme Q10) is a naturally occurring coenzyme found in palm oil. The concentration of ubiquinone in crude palm oil is determined in the range of 10–100 ppm (Hazura et al. 1990). Ubiquinone is found mostly in the inner mitochondrial membrane, especially in the heart, liver, kidney and pancreas. It plays an important role in the mitochondrial electron transport chain and is also a powerful antioxidant and free radical's scavenger, and it is believed to possess membrane-stabilising properties. Since its discovery, ubiquinone has been used to aid in the treatment of many cardiovascular diseases such as congestive heart failure, cardiac arrhythmias and hypertension.

Phospholipids are essential for cell membrane repair, optimum mental function (it provides vital neurotransmitter precursor) and lipid metabolism. Phospholipids (phosphatides) are indispensable components of cell membranes and are also natural emulsifiers, helping fats dissolve in water. They support a healthy cardiovascular system and have been used as a fat emulsifier in preventing arteriosclerosis, cardiovascular disease, brain function, and proper nerve function and maintain proper electrical energy and nutrients transfer across the cell membrane.

A number of patents have been filed on the recovery of carotenes from palm oil. These include U.S. Pat. No. 5,157,132, GB2160874, U.S. Pat. No. 6,072,092 and EP0349138. The recovery processes employ esterification/transesterification, molecular distillation, adsorbent at some stages. The current process is an advanced process integrating steps of at least one stage vacuum distillation, various physical and chemical treatment and purification to the phytonutrients concentrates. The integrated process yields higher carotenes concentration enriched with ubiquinones in indigenous diacylglycerols; and phospholipids enriched fraction.

SUMMARY OF INVENTION

This present invention relates to a process for the recovery of carotene concentrates such as carotenes, ubiquinones, and phospholipids from natural esterified oils and fats has in particular but not exclusive to crude palm oil and palm oil products.

This process involves the integration steps of (i) at least one stage vacuum distillation at temperatures ranging 80° C.–220° C. and pressure less than 40 mTorr; (ii) various physical and chemical treatment including filtration, solvent partitioning, saponification re-transesterification; and (iii) purification of phytonutrients containing concentrate.

Esterification/transesterification of crude palm oil and degummed and bleached palm oil is carried out with alkyl alcohol in the presence of an alkaline catalyst under conditions sufficient to convert free fatty acids and acylglycerols into alkyl esters-rich layer is either subjected to another re-transesterification process or clean water wash for neutralisation. The esterified palm oil is subjected to one or multi-stage vacuum distillation.

After first vacuum distillation, the carotenes enriched alkyl esters (residue) is subjected to the re-transesterification process. The process is carried out with alkyl alcohol with catalyst dissolving in alcohol or clean water under sufficient conditions to convert the traces of acylglycerols into alkyl esters and glycerol. The re-transesterified alkyl esters-rich layer is then subjected to second vacuum distillation for the production of carotenes concentrate.

In some instances, the esterified and or re-esterified palm oil is subjected to one stage vacuum distillation, yielding a concentrate residue enriched in carotenes.

The carotenes enriched alkyl esters layer from the first vacuum distillation is filtered or treated with hydrocarbon solvent to remove monoacylglycerols. The filtrate is subjected to second vacuum distillation for the production of carotenes concentrate.

Mixture of carotenes concentrate could also be produced by second stage vacuum distillation alone under conditions without going through third stage vacuum distillation.

A minimum amount of palm oil ethyl esters is added to the treated carotenes enriched alkyl esters (methyl esters in this case) prior to further vacuum distillation. Carotenes concentrate produced is enriched with ubiquinones in diacylglycerols with phospholipids. Treatment of carotenes concentrate is carried out using hydrophobic and hydrophilic solvents for further purification. The concentrate could be saponified to obtain desire concentration of carotenes fractions. Phospholipids are also recovered by membrane filtration of crude palm oil prior to conversion of oil into alkyl esters.

This present invention has many advantages. It is an integrated process where carotenes are recovered from crude palm oil, and, degummed and bleached palm oil. Carotenes recovered from this process present in diacylglycerols which is an effective carrier and dietary oil. With the improved two stage vacuum distillation, various treatments can be incorporated between the distillation stages. For instance, indigenous monoacylglycerols can be removed from the residue of first vacuum distillation after ten times of concentration and recovered as a high purity co-product. Other valuble minor components, ubiquinone and phospholipids are being concentrated in carotenes concentrate during the process.

DETAILED DESCRIPTION OF THE INVENTION

EXAMPLE 1

Crude palm oil (CPO) was esterified by using sodium hydroxide as catalyst with methanol to produce CPO methyl ester (ME). Glycerol was drained and CPOME was washed with hot distilled water. The neutralised CPOME was subjected to molecular distillation at temperature of 110° C., wiper speed of 250 rpm and pressure of 5 mTorr. Residue and distillate were collected for analysis of carotenes content. The carotenes concentration was 6.5% with recovery of 80.5%. Detail results are shown in the Table 1.

EXAMPLE 2

Bleached and degummed palm oil (BDPO) was esterified by using sodium hydroxide with methanol to produce BDPO methyl ester (ME). Glycerol was drained and BDPOME was washed with hot distilled water. The neutralized BDPOME was subjected to molecular distillation at temperature of 130° C., wiper speed of 250 rpm and pressure of 5 mTorr. Residue and distillate were collected for analysis of carotenes content. The carotenes concentration was 12.9% with recovery of 92.5% was obtained. Detailed results are shown in the Table 2.

EXAMPLE 3

Crude palm oil (CPO) was esterified by using sodium hydroxide with methanol to produce CPO methyl ester (ME). Glycerol was drained and CPOME was washed with hot distilled water. The neutralised CPOME was subjected to molecular distillation at temperature of 150° C., wiper speed of 300 rpm and pressure of 30 mTorr. All samples were analysed for carotenes content. The carotenes concentration was 5.9% with recovery of 79.9%. Detail results are shown in the Table 3.

EXAMPLE 4

Bleached and degummed palm oil (BDPO) was esterified by using sodium hydroxide with methanol to produce BDPO methyl ester (ME). Glycerol was drained and BDPOME was washed with hot distilled water. The neutralized BDPOME was subjected to molecular distillation at temperature of 150° C., wiper speed of 250 rpm and pressure of 5 mTorr. Residue was collected and analysed for carotenes content. The carotenes concentration was 8.5% with recovery of 91.7%. Detailed results are shown in the Table 4.

EXAMPLE 5

Bleached and degummed palm oil (BDPO) was esterified by catalytic reaction with methanol to produce BDPO methyl ester (ME). Glycerol was drained and BDOME was washed with hot distilled water. The neutralised BDOME was subjected to $1^{st}$ molecular distillation at temperature of 110° C., wiper speed of 250 rpm and pressure of 3 mTorr. Residue was subjected to $2^{nd}$ molecular distillation at temperature of 150° C., wiper speed of 250 rpm and pressure of 3 mTorr. All samples were analysed for carotenes content. The carotenes concentration was 8.6% with recovery of 86%. Detail results are shown in the Table 5.

EXAMPLE 6

Crude palm oil (CPO) was esterified by catalytic reaction with methanol to produce CPO methyl ester (ME). Glycerol was drained and CPOME was washed with hot distilled water. The neutralised CPOME was subjected to fast speed molecular distillation at temperature of 90° C., wiper speed of 250 rpm and pressure of 20 mTorr. Residue was re-transesterified to obtain higher degree of methyl esters conversion. The re-transesterification was carried out using sodium methylate as the catalyst. Treated sample was subjected to $2^{nd}$ molecular distillation at temperature of 150° C., wiper speed of 250 rpm and pressure of 3 mTorr. The samples were analysed for carotenes and ubiquinone content. The carotenes concentration was 14.4% with recovery of 92.7% and ubiquinone concentration was 0.3% with recovery of 94.7%. Detail results are shown in the Table 6.

EXAMPLE 7

Bleached and degummed palm oil (BDPO) was esterified by catalytic reaction with methanol to produce BDPO methyl ester (ME). Glycerol was drained and BDPOME was washed with hot distilled water. The neutralised BDPOME was subjected to fast speed molecular distillation at temperature of 90° C., wiper speed of 200 rpm and pressure of 20 mTorr. Residue was treated with hexane (1:1, v/v) and chilled to 0° C. for two hours. The mixture was filtered and pumped dried. Treated residue was subjected to $2^{nd}$ molecular distillation at temperature of 150° C., wiper speed of 250 rpm and pressure of 5 mTorr. All samples were analysed for carotenes content. The carotenes concentration was 12.2% with recovery of 87.9%. Detailed results are shown in the Table 7.

EXAMPLE 8

Crude palm oil (CPO) was esterified by catalytic reaction with methanol to produce CPO methyl ester (ME). Glycerol was drained and CPOME was washed with hot distilled water. The neutralised CPOME was subjected to fast speed molecular distillation at temperature of 90° C., wiper speed of 200 rpm and pressure of 20 mTorr. Residue was treated with hexane (1:1, v/v) and chilled to 0° C. for two hours. The mixture was filtered and washed with MeOH/$H_2O$ (5:2.5:0.5,v/v/v) for two times followed by vacuum pumped dried. Treated sample was subjected to $2^{nd}$ molecular distillation at temperature of 150° C., wiper speed of 250 rpm and pressure of 5 mTorr. Al 1 samples were analysed for carotenes content. The carotenes concentration was 18.1% with recovery of 87.9%. Detailed results are shown in the Table 8.

EXAMPLE 9

Crude palm oil (CPO) was esterified by catalytic reaction with methanol to produce CPO methyl ester (ME). Glycerol was drained and CPOME was washed with hot distilled water. The neutralised CPOME was subjected to fast speed molecular distillation at temperature of 90° C., wiper speed of 200 rpm and pressure of 20 mTorr. Residue was treated with iso-octane (1:1, v/v) and chilled to 0° C. for two hours.

The mixture was filtered and pumped dry. Treated sample was subjected to $2^{nd}$ molecular distillation at temperature of 150° C., wiper speed of 250 rpm and pressure of 5 mTorr. All samples were analysed for carotenes content. The carotenes concentration was 11.0% with recovery of 88.3%. Detail results are shown in the Table 9.

EXAMPLE 10

Crude palm oil (CPO) was esterified by catalytic reaction with methanol to produce CPO methyl ester (ME). Glycerol was drained and CPOME was washed with hot distilled water. The neutralised CPOME was subjected to fast speed molecular distillation at temperature of 90° C., wiper speed of 200 rpm and pressure of 20 mTorr. The residue was then subjected to re-esterification process, 50 g of the concentrate was re-transesterified with 1% alkaline catalyst (NaOH) dissolved in 20 ml methanol. The mixture was refluxed at 60–65° C. for 100 minutes. The sample of the re-esterification process was analysed for total carotenes, esters, acylglycerols and other minor components. The results of the analysis were shown in Table 10.

EXAMPLE 11

The CPOME produced subjected to similar process to that of Example 10. The product produced was then subjected to re-esterification process, 50 g of the concentrate was re-transesterified with 1% sodium hydroxide dissolved in 5 ml distilled water. The mixture was refluxed at 60–65° C. for 30 minutes. The sample of the re-esterification process was analysed for total carotenes, esters, acylglycerols and other minor components. The results of the analysis were shown in Table 11.

EXAMPLE 12

Residue from fast speed molecular distillation of CPOME (Example 8) was added with 10% (v/v) CPO ethyl esters. The mixture was subjected to $2^{nd}$ molecular distillation at temperature of 150° C., wiper speed of 250 rpm and pressure of 1 mTorr. The mass flow rate of the mixture in the distillation processes has increased 3 times of the normal flow rate without addition of ethyl esters. All samples were analysed for carotenes content. The carotenes concentration was 12.8% with recovery of 87.4%. Detailed results are shown in Table 12.

EXAMPLE 13

5.0 g of carotenes concentrate was subjected to unsaponification with 7.0 ml of 10% potassium hydroxide in 30.0 ml of ethanol. The mixture was refluxed for ½ hour. The reacted mixture was transferred to a separating funnel and the unsaponifiable matters were extracted with 50 ml of hexane: distilled water (90:10, v/v) for 3 times. The extracts were neutralised with copious of 10% ethanol in distilled water. The neutralised extract was then vacuum pumped dry and analysed. The results of the analysis are shown in Table 13.

EXAMPLE 14

Carotenes concentrate (from Example 8) was used as crude material in the treatment. 0.1 g of carotenes concentrate was added to 1 ml of Hexane and 3 ml of Methanol. The mixture was chilled to −10° C. for 1 hour. The top and bottom layers were separated and vacuum pumped dried. Samples were analysed for total carotenes content. The carotenes concentration was 30.1% with recovery of 69%. Detail results are shown in the Table 14.

EXAMPLE 15

Carotenes concentrate (from Example 8) was used as crude material in the treatment, 0.16 g of carotenes concentrate was added to 5 ml of Hexane and 10 ml of Methanol. The mixture was chilled to −10° C. for 1 hour. The top and bottom layers were separated and vacuum pumped dry. Samples were analysed for total carotenes content. The carotenes concentration was 24.3% with recovery of 84.7%. Detail results are shown in the Table 15.

EXAMPLE 16

Carotenes concentrate produced from examples 1, 3 and 4 were analysed for total phospholipids content. The results are shown in Table 16 with the concentration ranging from 0.60% to about 4.0%.

EXAMPLE 17

2 litres of CPO was filtered with a membrane filter with a 0.05 μm pore size. This process was carried out to reduce impurities in the CPO. These include phospholipids, iron and copper. The CPO was subjected to the membrane system with the temperature of 60° C., pressure of 2 bar with 300 rpm. The filtrate was analysed for total phospholipids. It was found that the total phospholipids could be reduced to 46.40 ppm from 171.17 ppm found in CPO.

EXAMPLE 18

500 g of neutralised palm oil (NPO) was esterified by sodium methylate with methanol to produce NPO methyl esters (ME). Glycerol was drained and the NPOME was divided into two portions for different neutralisation approaches. To the first part of NPOME, 10% of distilled water was used for each washing step until neutralised NPOME was obtained. To the second part of NPOME, hydrochloric acid was added into distilled water until pH 4–5. 10% of the acidified distilled water was then used for each washing step until NPOME was neutralised. The result shows that the acidified distilled water is better than normal distilled water for neutralization of NPOME produced by reducing the total amount of distilled water used by 40%. All minor components such as carotenes, vitamin E, phytosterols and squalene were preserved well in acidified water washing. The results are shown in Table 18.

TABLE 1

(Single Stage Distillation - No treatment)
Condition: 110° C., 250 rpm, 0.93 ml/min, 5 mTorr

| | Carotene | | |
|---|---|---|---|
| | ppm | mg | % Recovery |
| Feed: CPO Methyl Esters | 571.0 | 246.7 | 100.0 |
| Carotenes Concentrate | 65232.6 | 198.6 | 80.5 |

TABLE 2

(Single Stage Distillation - No treatment)
Condition: 130° C., 250 rpm, 0.93 ml/min, 5 mTorr

| | Carotene | | |
|---|---|---|---|
| | ppm | mg | % Recovery |
| Feed: BDPO Methyl Esters | 571.0 | 246.7 | 100.0 |
| Carotenes Concentrate | 129159.0 | 228.2 | 92.5 |

TABLE 3

(Single Stage Distillation - No treatment)
1st Distillation: 150° C., 300 rpm, 0.93 ml/min, 30 mTorr

| | Carotene | | |
|---|---|---|---|
| | ppm | mg | % Recovery |
| Feed: CPO Methyl Esters | 698.0 | 603.1 | 100.0 |
| Carotenes Concentrate | 58695.0 | 481.8 | 79.9 |

TABLE 4

(Single Stage Distillation - No treatment)
1st Distillation: 150° C., 250 rpm, 0.93 ml/min, 5 mTorr

| | Carotene | | |
|---|---|---|---|
| | ppm | mg | % Recovery |
| Feed: BDPO Methyl Esters | 571.0 | 246.7 | 100.0 |
| Carotenes Concentrate | 84819.0 | 226.2 | 91.7 |

TABLE 5

(Two Stage Distillation - No treatment)

| | Carotene | | |
|---|---|---|---|
| | ppm | mg | % Recovery |
| 1st Distillation: 110° C., 250 rpm, 0.9 ml/min, 3 mTorr | | | |
| Feed: BDPO Methyl Estesr | 612.0 | 3172.6 | 100.0 |
| Carotenes enriched alkyl esters | 47174.0 | 2959.1 | 93.3 |
| 2nd Distillation: 150° C., 250 rpm, 0.93 ml/min, 3 mTorr | | | |
| Carotenes enriched alkyl esters | 47174.0 | 2794.4 | 100.0 |
| Carotenes Concentrate | 86625.0 | 2402.5 | 86.0 |

TABLE 6

(Two Stage Distillation - Re-transesterification of concentrate after 1st Distillation)

1st Distillation: 90° C., 200 rpm, 2.2 ml/min, 20 mTorr

| | Carotene | | |
|---|---|---|---|
| | ppm | mg | % Recovery |
| Feed: CPO Methyl Esters | 682.0 | 4124.7 | 100.0 |
| Carotenes enriched alkyl esters | 6796.0 | 4022.1 | 97.5 |

2nd Distillation: 150° C., 250 rpm, 0.93 ml/min, 3 mTorr

| | Carotene | | | Ubiquinone | | |
|---|---|---|---|---|---|---|
| | ppm | mg | % Recovery | ppm | mg | % Recovery |
| Feed: Treated carotenes enriched alkyl esters | 6790.0 | 2933.3 | 100.0 | 140 | 60.5 | 100.0 |
| Carotenes Concentrate | 143123.0 | 2720.5 | 92.7 | 3014.0 | 57.3 | 94.7 |

TABLE 7

(Two Stage Distillation - Treatment with Hexane)

| | Carotene | | |
|---|---|---|---|
| | ppm | mg | % Recovery |
| 1st Distillation: 90° C., 200 rpm, 2.2 ml/min, 5 mTorr | | | |
| Feed: BDPO Methyl Esters | 571.0 | 2466.7 | 100.0 |
| Carotenes enriched alkyl esters | 3949.4 | 2149.7 | 87.1 |
| 2nd Distillation: 150° C., 250 rpm, 0.93 ml/min, 7 mTorr | | | |
| Feed: Treated carotenes enriched alkyl esters | 3949.4 | 1023.7 | 100.0 |
| Carotenes Concentrate | 121825.0 | 900.2 | 87.9 |

TABLE 8

(Two Stage Distillation - Treatment with Hexane and MeOH/H₂0 Washing)

| | Carotene | | |
|---|---|---|---|
| | ppm | mg | % Recovery |
| 1st Distillation: 90° C., 200 rpm, 2.2 ml/min, 20 mTorr | | | |
| Feed: CPO Methyl Esters | 571.0 | 2466.7 | 100.0 |
| Carotenes enriched alkyl esters | 4991.5 | 2630.7 | 98.3 |
| 2nd Distillation: 150° C., 250 rpm, 0.93 ml/min, 5 mTorr | | | |
| Feed: Carotenes enriched alkyl esters | 4991.5 | 1293.8 | 100.0 |
| Carotenes Concentrate | 181075.6 | 1134.7 | 87.7 |

TABLE 9

(Two Stage Distillation - Treatment with Iso-Octane)

| | Carotene | | |
|---|---|---|---|
| | ppm | mg | % Recovery |
| 1st Distillation: 90° C., 200 rpm, 2.2 ml/min, 5 mTorr | | | |
| Feed: CPO Methyl Esters | 602.0 | 2340.6 | 100.0 |
| Carotenes enriched alkyl esters | 3720.0 | 2105.2 | 89.9 |
| 2nd Distillation: 150° C., 250 rpm, 0.93 ml/min, 5 mTorr | | | |
| Feed: Treated carotenes enriched alkyl esters | 3720.0 | 964.2 | 100.0 |
| Carotenes Concentrate | 110481.0 | 851.8 | 88.3 |

TABLE 10

(Re-transesterification of carotenes enriched alkyl esters after first stage distillation-catalyst dissolved in methanol)

| | Percentage (%) | | | | | |
|---|---|---|---|---|---|---|
| | Esters | MG | DG | TG | Carotenes | Others Minor Components |
| CPO Methyl esters | 99.413 | 0.296 | 0.043 | N.D. | 0.071 | 0.177 |
| Carotenes enriched alkyl esters | 96.730 | 0.876 | 0.509 | N.D. | 0.632 | 1.253 |
| Treated carotenes enriched alkyl esters | 98.032 | 0.274 | N.D. | N.D. | 0.609 | 1.085 |

Note:
MG: Monoacylglycerol
DG: Diacylglycerol
TG: Triacylglycerol
N.D.: Non-detectable
CPO: Crude Palm Oil
BDPO: Bleached and Degummed Palm Oil
Other Minor Components: Squalene, Sterols, Tocols (tocopherols and tocotrienol)

TABLE 11

(Re-transesterification of carotenes enriched alkyl esters after first stage distillation-catalyst dissolved in treated water)

| | Percentage (%) | | | | | |
|---|---|---|---|---|---|---|
| | Esters | MG | DG | TG | Carotenes | Others Minor Components |
| CPO Methyl esters | 99.413 | 0.296 | 0.043 | N.D. | 0.071 | 0.177 |
| Carotenes enriched alkyl esters | 96.730 | 0.876 | 0.509 | N.D. | 0.6320.632 | 1.253 |
| Treated carotenes enriched alkyl esters | 97.740 | 0.263 | 0.019 | N.D. | 0.622 | 1.357 |

TABLE 12

(Two Stage Distillation-with addition of ethyl esters)
2nd Distillation: 150° C., 250 rpm, 1 mTorr, 3 ml/min

| | Carotenes | | |
|---|---|---|---|
| | ppm | mg | % Recovery |
| Feed: CPO Methyl Esters + 10% Ethyl Esters | 4991.5 | 998.3 | 100 |
| Carotenes Concentrate | 128120 | 872.7 | 87.4 |

TABLE 13

(Saponification of carotenes concentrate)

| | Percentage (%) | | | | | | |
|---|---|---|---|---|---|---|---|
| | FFA | Esters | MG | DG | TG | Carotenes | Others |
| Carotenes Concentrate | 1.45 | 1.11 | 34.61 | 18.26 | 33.19 | 2.10 | 9.28 |
| Unsaponified Sample | 24.42 | 0.00 | 0.00 | 13.92 | 34.95 | 11.58 | 15.13 |

TABLE 14

(Partition of carotenes)

| | Carotenes | | |
|---|---|---|---|
| | ppm | mg | % Recovery |
| Carotenes Concentrate | 170982 | 0.0172 | 100.0 |
| Hexane Layer | 301060 | 0.0119 | 69.0 |
| Methanol Layer | 58556 | 0.0036 | 30.2 |

TABLE 15

(Partition of carotenes)

| | Carotenes | | |
|---|---|---|---|
| | ppm | mg | % Recovery |
| Carotenes Concentrate | 170982 | 0.0278 | 100.0 |
| Hexane Layer | 243538 | 0.0235 | 84.7 |
| Methanol Layer | 41274 | 0.0027 | 11.6 |

TABLE 16

| | Phospholipids (%) |
|---|---|
| Carotenes Concentrate (from Example 1) | 1.78 |
| Carotenes Concentrate (from Example 3) | 3.83 |
| Carotenes Concentrate (from Example 4) | 0.78 |

TABLE 18

| | Concentration (ppm) | |
|---|---|---|
| | Carotenes | Vitamin E |
| Neutralised Palm Oil | 512 | 950 |
| Acidified distilled water washed NPOME | 508 | 908 |
| Normal distilled water washed NPOME | 500 | 921 |

The invention claimed is:

1. A process to recover carotene concentrates comprising the steps of:
   i) subjecting alkyl esters produced from palm oil to at least one stage vacuum distillation at temperature ranging from 80–220° C. and pressure at less than 40 mTorr to yield phytonutrients concentrate in residue;
   ii) separation of polar lipids and other impurities from the residue in step (i);
   iii) subjecting the treated residue from step (ii) to a second vacuum distillation wherein residue from the distillation contain carotenes concentrates consisting carotenes; ubiquinones and phospholipids.

2. A process to recover carotene concentrates claimed in claim 1 wherein the second vacuum distillation is carried out at temperature ranging from 80° C. to 200° C. and at pressure less than 40 mTorr.

3. A process to recover carotene concentrates as claimed in claim 1 wherein the separation of polar lipids and other impurities in step (ii) is done in any one of the ways consisting of:
   i) treating the residue in step (i) of claim 1 with a hydrocarbon solvent with or without subsequent alkyl alcohol/treated water purification to remove the monoacylglycerols; or
   ii) re-transesterifying the residue in step (i) of claim 1 using alkaline catalysts to convert the traces of acylglycerols into alkys esters and glycerol; or
   iii) direct filtration of residue in step (i) of claim 1 under vacuum.

4. A process to recover carotene concentrates as claimed in claim 3 wherein the mixture in step (i) is chilled down to low temperature for at least 2 hours and monoacylglycerls is separated from the residue.

5. A process to recover carotene concentrates as claimed in claim 3 wherein alkaline catalyst used in the re-transesterification in step (ii) is selected from a group consisting of such as sodium hydroxide, potassium hydroxide and sodium methylate in the presence of short and branched alkyl alcohol such as methanol and ethanol.

6. A process to recover carotene concentrates as claimed in claim 3 wherein 2% of palm oil ethyl esters are added to the treated residue in step (iii) prior to subsequent vacuum distillation.

7. A process to recover carotene concentrates as claimed in claim 1 wherein the carotenes concentrate is further purified by either:
   i) adding alkaline catalysts in presence of alkyl alcohol such as potassium hydroxide in ethanol; or
   ii) adding hydrocarbon solvent and alkyl alcohol and chilled to −10° C. for at least one hour to partition the carotenes into hydrocarbon layer.

8. A process to recover carotene concentrates as claimed in claim 3 or 7 wherein the hydrocarbon solvents used are hexane or iso-octane and the alkyl alcohols used are short and branched alkyl alcohols such as methanol and ethanol.

9. A process to recover carotene concentrates as claimed in claim 1 wherein the alkyl esters is produced from the crude palm oil or treated palm oil such as bleached and degummed palm oil and membrane filtered palm oil.

10. A process to recover carotene concentrates as claimed in claim 9 wherein the removal of excess of alkaline catalyst in alkyl esters produced is carried out by using acidified water pH between 4–5.

* * * * *

UNITED STATES PATENT AND TRADEMARK OFFICE
CERTIFICATE OF CORRECTION

PATENT NO. : 7,141,712 B2 Page 1 of 1
APPLICATION NO. : 10/642597
DATED : November 28, 2006
INVENTOR(S) : Choo Yuen May et al.

It is certified that error appears in the above-identified patent and that said Letters Patent is hereby corrected as shown below:

Title Page, Item (75), Inventors:
"Yuen May Choo, Selengor (MY)"

should read:

--Yuen May Choo, Selangor (MY)--

Title Page, Item (30),

Foreign Application Priority Data

"June 20, 2002 (MY) .............PI 20023068"

Title Page should read:

Foreign Application Priority Data

--August 20, 2002 (MY)...........PI 20023068--

Column 12, Claim 4, LN. 33

"monoacylglycerls"

should read:

--monoacylglycerols--

Signed and Sealed this

Twenty-sixth Day of June, 2007

JON W. DUDAS
*Director of the United States Patent and Trademark Office*

UNITED STATES PATENT AND TRADEMARK OFFICE
CERTIFICATE OF CORRECTION

PATENT NO.        : 7,141,712 B2                                          Page 1 of 1
APPLICATION NO.   : 10/642597
DATED             : November 28, 2006
INVENTOR(S)       : Choo Yuen May et al.

It is certified that error appears in the above-identified patent and that said Letters Patent is hereby corrected as shown below:

Col. 1, Ln 25, Delete "retinal" and insert -- retinol --.

Signed and Sealed this

Fifteenth Day of July, 2008

JON W. DUDAS
*Director of the United States Patent and Trademark Office*